United States Patent [19]

Ogiu

[11] 4,181,131
[45] Jan. 1, 1980

[54] HIGH FREQUENCY ELECTROSURGICAL INSTRUMENT FOR CUTTING HUMAN BODY CAVITY STRUCTURES

[75] Inventor: Hisao Ogiu, Hachioji, Japan
[73] Assignee: Olympus Optical Co., Ltd., Tokyo, Japan
[21] Appl. No.: 880,347
[22] Filed: Feb. 23, 1978

[30] Foreign Application Priority Data

Feb. 28, 1977 [JP] Japan .................................. 52-21339
Feb. 28, 1977 [JP] Japan .................................. 52-21340

[51] Int. Cl.² .............................................. A61B 17/36
[52] U.S. Cl. ............................................... 128/303.15
[58] Field of Search .................. 128/303.14, 303.13, 128/303.15, 303.16, 303.17, 320

[56] References Cited

U.S. PATENT DOCUMENTS

| 958,753 | 5/1910 | Meyer | 128/303.14 X |
| 1,794,296 | 2/1931 | Hyams | 128/303.14 |
| 3,903,892 | 9/1975 | Komiya | 128/303.15 |

FOREIGN PATENT DOCUMENTS

| 2426781 | 12/1975 | Fed. Rep. of Germany | 128/303.15 |
| 2265344 | 10/1975 | France | 128/303.14 |
| 2275226 | 1/1976 | France | 128/303.17 |

Primary Examiner—Lee S. Cohen

[57] ABSTRACT

A high frequency electrosurgical instrument for cutting human body cavity structures comprises a sheath made of an electrically insulating material and a metal wire. The metal wire consists of an operating wire portion reciprocating through the sheath and a cutting wire portion folded back toward the sheath at the end of the operating wire portion extended from the distal end of the sheath. The end of the cutting wire portion which is remote from the end of the operating wire portion is held by the sheath and at least the part of the operating wire portion extensible from the distal end is covered with an electrically insulating wrapping member. After the distal end portion of the sheath of the instrument is conducted through the channel in an endoscope at human body cavity structures, the operating wire portion is extended from the distal end of the sheath and its extended portion is pulled by the cutting wire and curved so that the extended end portion of the wrapping member abuts against the inner wall of the human cavity and prevents other structures than those to be cut from being damaged by the cutting wire portion.

16 Claims, 22 Drawing Figures

FIG. 1 PRIOR ART
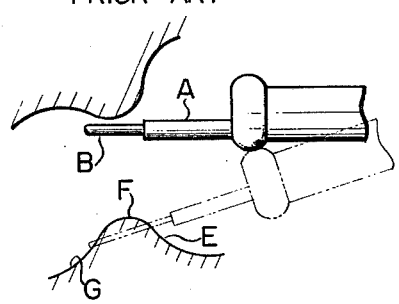
FIG. 2 PRIOR ART
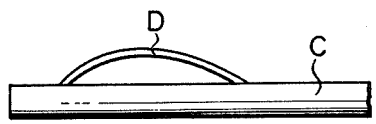
FIG. 3 PRIOR ART
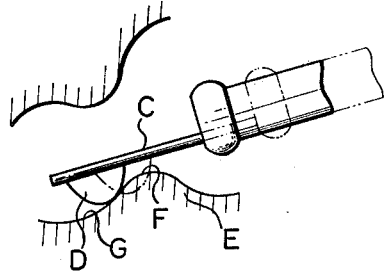
FIG. 4 PRIOR ART
FIG. 5
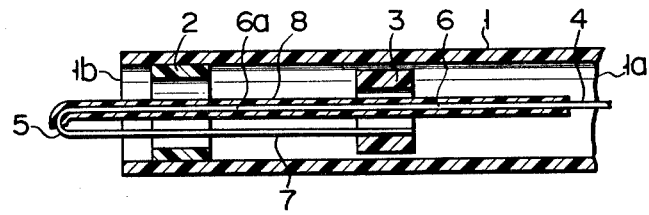
FIG. 6
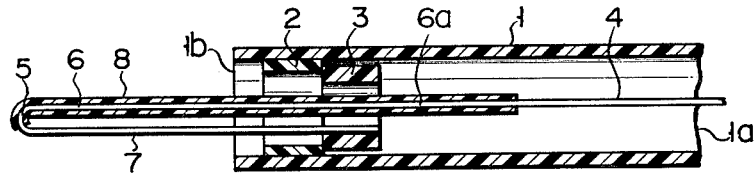

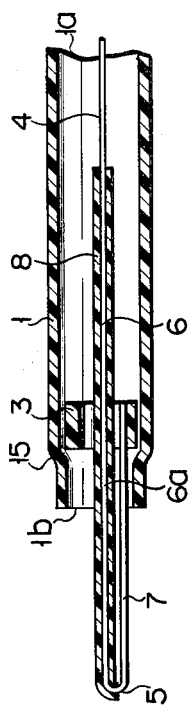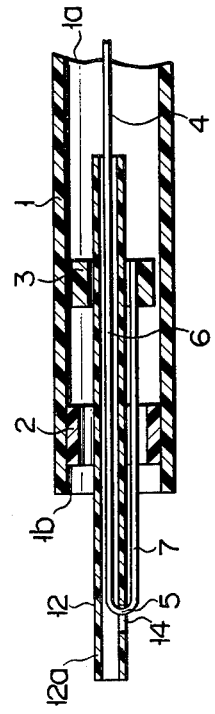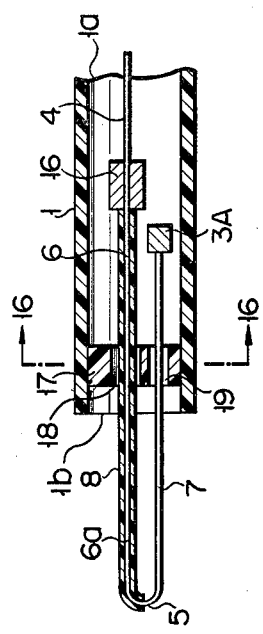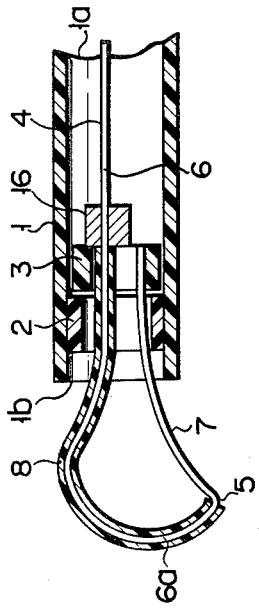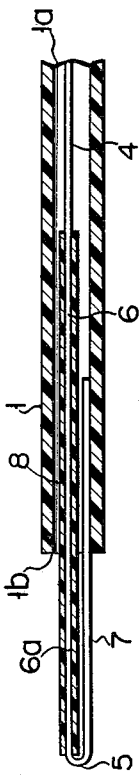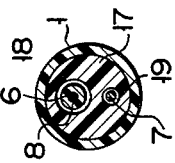

HIGH FREQUENCY ELECTROSURGICAL INSTRUMENT FOR CUTTING HUMAN BODY CAVITY STRUCTURES

BACKGROUND OF THE INVENTION

This invention relates to a high frequency electrosurgical instrument, and more particularly to a high frequency electrosurgical instrument which causes the cutting section of the instrument to be conducted exactly to that portion of a human body cavity structure which is going to be cut.

One known high frequency electrosurgical instrument is the type which, as shown in FIG. 1, comprises an electrically insulating tube or sheath A and a metal cutting blade B extensible from the distal end of the sheath A. After the distal end of the sheath A is conducted through an endoscope to that portion of a human body structure which is going to be cut, the cutting blade B is made, as shown in solid lines in FIG. 2, to protrude from the distal end of the sheath A. Therefore, the blade B is pressed, as shown in dot-dash lines in FIG. 2, against that portion E of a human body structure required to be cut, and cuts the portion E by introducing current through the blade B.

Another prior art high frequency electrosurgical instrument is the type which comprises, as shown in FIG. 3, a cutting wire D protruding in the arcuate form from the lateral side of the distal end portion of an electrically insulating tube sheath C. After the distal end portion of the sheath C is brought, as in the case of FIG. 1, to that portion E (FIG. 4) of a human body cavity structure being cut, the arcuate cutting wire D is made, as shown in FIG. 4, to protrude from the lateral side of the sheath C. The arcuate cutting wire D is pressed, as shown in dot-dash lines in FIG. 4, against that portion E of the human body cavity structure which is going to be cut. Thereafter, the sheath C is pulled back together with the arcuate cutting wire D, as shown in dot-dash lines in FIG. 4, to cut the portion E by introducing current through the wire D.

Since most of the portions E of a human body cavity structure being cut are so narrow as indicated by F in FIGS. 2 and 4, portions behind the narrow portion F can be little observed by an endoscope. Therefore, even where the tip of the cutting blade B or arcuate cutting wire D touches or depresses that portion G of a human body cavity structure or mucous membrane which lies behind the narrow portion F and should not be cut, it sometimes happens that an operator who is unaware of this fact cuts the portion G. Further, where a cutting instrument is pressed against that portion of a human body cavity structure which is going to be cut, an endoscope or the cutting instrument itself is generally made to swing, presenting difficulties in controlling the extent of cutting, with the possibility of said cutting being carried to excess.

SUMMARY OF THE INVENTION

An object of this invention is to provide a high frequency cutting instrument which easily and reliably cuts a particularly narrow portion of a human body cavity structure requiring incision without unnecessarily cutting the surroundings of said portion, particularly that part of the human body cavity structure or mucous membrane which lies behind the spot of incision.

According to an aspect of this invention, there is provided a high frequency cutting instrument for cutting a human body cavity structure, which comprises a sheath made of electrically insulating material; a metal operating wire which reciprocates through the sheath and whose distal end is made to protrude from a distal end of the sheath; a wrapping member prepared from electrically insulating material to enclose the distal end of the operating wire; and a cutting wire which is integrally formed at the distal end of the operating wire and folded back from said distal end toward the sheath and whose end remote from the distal end of the operating wire is held by the sheath.

This invention offers the advantages that when protruding from the distal end of the sheath, the distal end of the operating wire is made arcuate; the whole wrapping member enclosing the protruding end of the operating wire protects those portions of a human body cavity which should not be cut; and particularly the end of the wrapping member of the distal end of the operating wire abuts against those portions of the human body cavity structure which should not be cut, thereby only allowing those portions of the human body cavity structure which substantially need cutting to be incised.

BRIEF DESCRIPTION OF THE DRAWING

FIG. 1 is a side view of the main part of one known high frequency cutting instrument;

FIG. 2 indicates the manner in which the cutting instrument of FIG. 1 is operated;

FIG. 3 is a side view of the main part of another known high frequency cutting instrument;

FIG. 4 illustrates the manner in which the cutting instrument of FIG. 3 is operated;

FIG. 5 is a longitudinal sectional view of the main part of a high frequency cutting instrument according to one embodiment of this invention;

FIG. 6 is a longitudinal sectional view of the high frequency cutting instrument of FIG. 5 while an operating wire is being brought forward;

FIGS. 11 to 15 are respectively the longitudinal sectional views of high frequency cutting instruments according to other embodiments of the invention;

FIG. 16 is a sectional view on line 16—16 of FIG. 15;

FIG. 17 is a longitudinal sectional view of a high frequency cutting instrument according to still another embodiment of the invention;

DETAILED DESCRIPTION OF THE PREFERRED EMBODIMENTS

Figure 7:
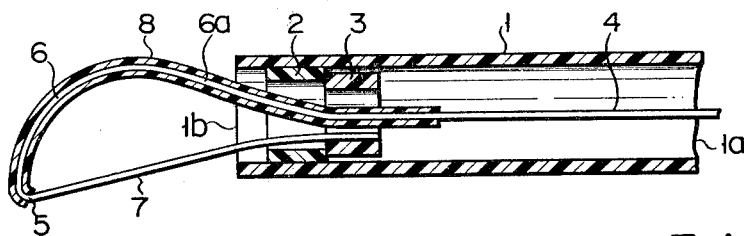
FIG. 7 is a longitudinal sectional view of the high frequency cutting instrument of FIG. 5 where an operating wire is set in a state ready for cutting.
Figure 8:
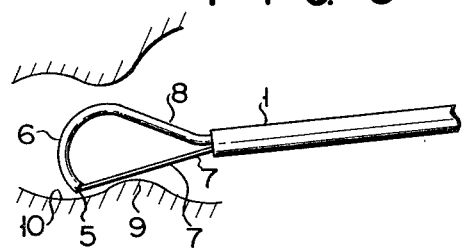
FIG. 8 shows the condition in which the cutting instrument of FIG. 6 is applied in cutting.

Referring to FIGS. 5 to 7, a sheath 1 prepared from electrically insulating material, for example, synthetic resin is guided through the narrow channel (not shown) of an endoscope as narrow as 2.8 to 7 mm. A ring-shaped or tubular stop 2 is fixed on the inner wall of the distal end of the sheath 1. A ring-shaped engagement member 3 having a larger outer diameter than the inner diameter of the stop 2 is received in the sheath 1 to be reciprocable in the axial direction thereof. The sheath 1 further contains a metal wire 4 made of, for example, stainless steel strands (for example, 0.3 to 0.4 mm in diameter) and extended from the proximal end 1a to the distal end 1b of the sheath 1. That portion of the metal wire 4 which protrudes from the distal end of the sheath 1 is folded backward. The tip of said bent end portion of the metal wire 4 is fixed to the ring-shaped engagement member 3. With this invention, that section of the metal wire 4 which is defined between the proximal end 1a of the sheath 1 and the bend 5 of the metal wire 4 is referred to as "an operating wire 6," and that folded portion of the metal wire 4 is referred to as "a cutting wire 7." The distal end portion 6a of the operating wire 6 which can protrude from the distal end 1b of the sheath 1 is covered with a wrapping layer or tubular member 8 (hereinafter referred to as "a protecting member") made of flexible electrically insulating material such as tritetrafluoroethylene resin (hereinafter referred to as Teflon which is a trade mark). In constrast, the cutting wire 7 remains uncovered. Where the operating wire 6 is controlled at the side of the proximal end 1a to be shifted from the state in which the wire 6 is received in the sheath 1 to an advancing state, the bend 5 of the operating wire 6 protrudes from the distal end 1b of the sheath 1. When the operating wire 6 is brought to a state shown in FIG. 6, the engagement member 3 abuts against the stop 2. When further moved forward, the operating wire 6 is pulled by the cutting wire 7, causing the protruding end of the operating wire 6 to be made arcuate. Where, under the condition of FIG. 7, current is introduced with the cutting wire 7 pressed, as shown in FIG. 8, against a human body cavity structure 9 being cut (more generally, a specified narrow portion of the human body cavity structure), the tip of the protecting member 8 at the bend 5 touches that portion 10 of the body cavity structure or mucous membrane which lies behind the structure 9 of incision. Therefore, the cutting of the structure 9 can be effected without hurting the contact portion 10 or at least deeply cutting it by mistake.

Figure 9:
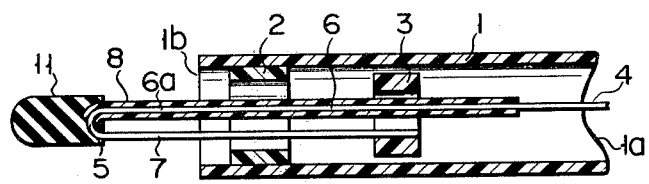
FIG. 9 is a longitudinal sectional view of a high frequency cutting instrument according to another embodiment of the invention.
Figure 10:
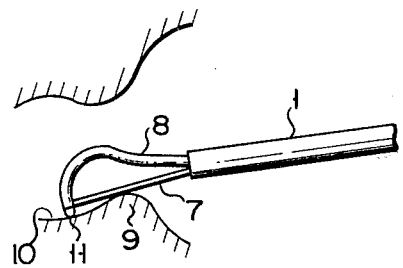
FIG. 10 shows the manner in which the high frequency cutting instrument of FIG. 9 is operated.

In the embodiment of FIG. 9, a round-headed cylindrical abutment 11 made of electrically insulating material, for example, rubber is projectively fitted to the bend 5 of a wire 4. When a cutting wire 7 is pressed, as shown in FIG. 10, against a human body cavity structure or narrow portion or spot 9 which should be cut, the free end of the abutment 11 contacts that portion 10 of a human body cavity structure or mucous membrane which lies behind the aforesaid spot 9 of incision and can not be observed by an endoscope. Therefore, only the required spot 9 is cut, preventing the neighboring portion 10 from being hurt or cut by mistake.

Figure 11:
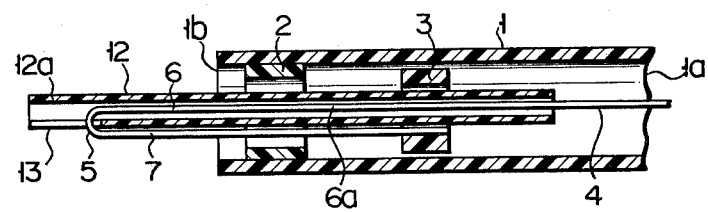

Referring to the embodiment of FIG. 11, the distal end portion 6a of an operation wire 6 which can be made to protrude from the distal end 1b of a sheath 1 is inserted into a protecting tube 12 made of flexible, electrically insulating material, for example, Teflon. The bend 5 of the operating wire 6 is held in a slit or cut 13 made slightly narrower than a cutting wire 7 and formed in the protecting tube 12 to extend lengthwise from the distal end thereof, thereby preventing the cutting wire 7 from coming off the protecting tube 12.

Referring to the embodiment of FIG. 12, the slit or cut 13 of the protecting tube 12 of FIG. 11 is replaced by a small hole 14. The folded portion or bend 5 of the operating wire 6 is disposed in the hole 14. This arrangement also prevents the cutting wire 7 from coming off the protecting tube.

In the embodiment of FIGS. 11 and 12, the tip of the distal end portion 12a of the Teflon tube 12 is pressed, like the abutment 11 of FIG. 9, against the portion of a human body cavity structure or mucous membrane which lies behind a spot of incision. Therefore, the distal end portion 12a performs exactly the same function as the abutment 11.

Throughout the foregoing embodiments, a ring-shaped stop 2 was formed on the inner wall of the distal end portion 1b of the sheath 1. As shown in FIG. 13, however, it is possible to reduce the diameter of the distal end portion 1b, thereby forming a stepped portion 15 and cause the ring-shaped engagement member 3 holding the leading end of the cutting wire 7 to be engaged with the stepped portion 15. This arrangement eliminates the necessity of providing the aforesaid ring-shaped stop 2.

In the embodiment of FIG. 14, an abutment 16 is fixed to the intermediate portion of an operating wire 6 extending from a ring-shaped engagement member 3 to the proximal end 1a of a sheath 1. Where, under this arrangement, the operating wire 6 is moved forward from the proximal end 1a of the sheath 1 at the time of cutting, the ring-shaped engagement member 3 is first brought to rest in contact with a stop 2 and then the abutment 16 is pressed against the engagement member 3. This arrangement restricts the extent to which the operating wire 6 protrudes from the distal end 1b of the sheath 1, enabling the leading end portion of the operating wire 6 always to take an arcuate form of a fixed size.

Referring to FIGS. 15 and 16 jointly showing another embodiment of this invention, a ring shaped stop 17 formed on the inner wall of the distal end portion 1b of a sheath 1 is bored with a hole 18, which allows the passage of the operating wire 6 whose intermediate portion is fitted with the abutment 16 and a hole 19 which allows the passage of the cutting wire 7 whose free end is fitted with an engagement member 3A. As the operating wire 6 further proceeds, first the engagement member 3A and then the abutment 16 are pressed against the stop 17 to render the operating wire 6 arcuate. Since the operating wire 6 does not make any further advance after the engagement member 3A and abutment 16 contact the stop 17, the arcuate form of the leading end portion of the operation wire 6 remains unchanged, enabling a human body cavity structure or narrow portion to be cut just as required with great stability.

The embodiments of FIGS. 17, 19, 20 and 21 are particularly adapted to cut a human body cavity structure or narrow portion. High frequency electrosurgical instruments according to the embodiments of FIGS. 17, 19, 20 and 21 are applied by being conducted through a narrow channel like the channel 2.8 mm in diameter of an endoscope.

The embodiment of FIG. 17 represents the type in which the ring-shaped stop 2 and the engagement member 3 holding the free end of the cutting wire 7 are omitted from the embodiment of FIG. 5; and the free end of a cutting wire 7 is fixed to the inner wall of the distal end portion 1b of the sheath 1. This arrangement can reduce the diameter of the sheath 1, and simplify the construction of the whole electrosurgical instrument as will be easily understood.

Figure 18:
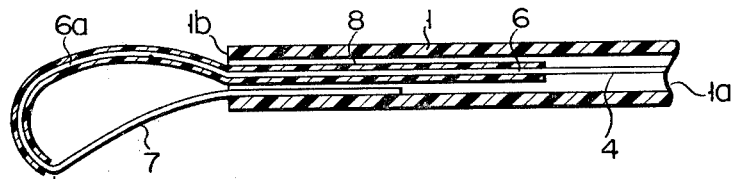
FIG. 18 is a longitudinal sectional view of the high frequency cutting instrument of FIG. 17 while an operating wire is being brought forward for application.

When the operating wire 6 is pushed from the proximal end 1a of the sheath 1. The distal end portion 6a of the operating wire 6 protruding from the distal end 1a of the sheath 1 takes, as illustrated in FIG. 18, an arcuate form just like that of FIGS. 7 and 8. Accordingly, the embodiment of FIG. 17 displays the same operation and effect as that of FIG. 5.

Figure 19:
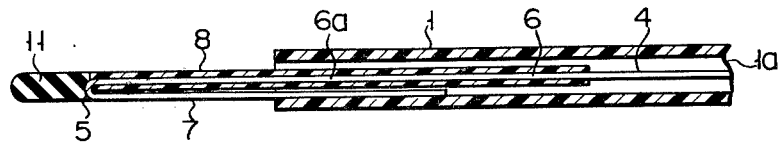
FIG. 19 is a longitudinal sectional view of a high frequency cutting instrument according to a further embodiment of the invention.

The embodiment of FIG. 19 is the type in which an electrically insulating, round-headed cylindrical abutment 11 made of, for example, rubber is fitted to the outer end of a protecting member 8 of FIG. 17 prepared from electrically insulating material. The embodiment of FIG. 19 is applied in the same manner as that of FIG. 10, indicating the same operation and effect as that of FIG. 9.

Figure 20:
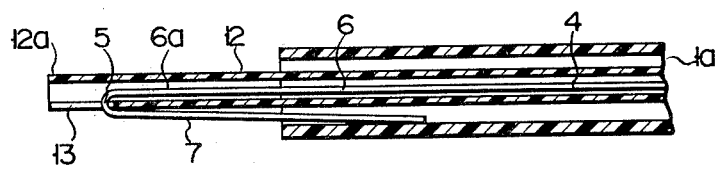
FIGS. 20 to 22 are respectively the longitudinal sectional views of high frequency cutting instruments according to still further embodiments of the invention.
Figure 21:
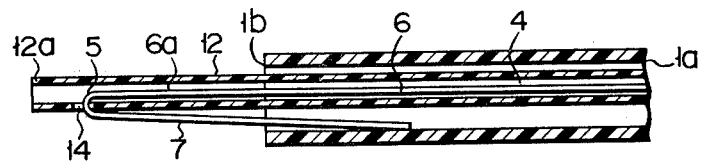

The embodiments of FIGS. 20 and 21 closely resemble those of FIGS. 11 and 12, except that the stop 2 and engagement member 3 are omitted, and the free end of the cutting wire 7 is fixed to the inner wall of the sheath 1. During application, the distal end 12a of a protecting tube 12 abuts against that portion of a human body cavity structure or narrow portion which lies behind a spot of incision, showing the same operation and effect as in the embodiment of FIGS. 11 and 12.

Figure 22:
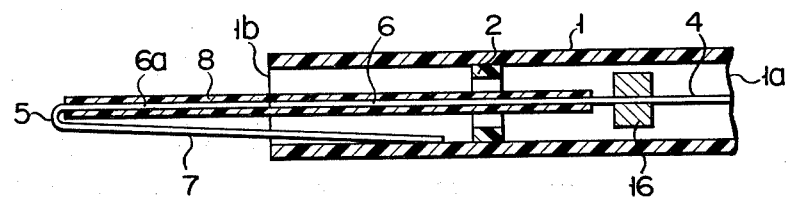

The embodiment of FIG. 22 is adapted for the case where a sheath 1 has a larger diameter than in the embodiments of FIGS. 17 to 21. A ring-shaped stop 2 is fixed to the inner wall of the distal end portion 1b of the sheath 1. An operating wire 6 of a metal wire 4 penetrates the sheath 1 and stop 2. The intermediate portion of the operating wire 6 is fitted with an abutment 16 whose outer diameter is larger than the inner diameter of the stop 2. When the abutment 16 is pressed against the stop 2, the extent to which the distal end portion 6a of the operating wire 6 protrudes from the distal end 1b of the sheath 1 is restricted. A cutting wire 7 constituted by that portion of the metal wire 4 which is folded back from the bend 5 toward the sheath 1 has its free end fixed to the inner wall of the distal end portion of the sheath 1. The distal end portion 6a of the operating wire 6 which is made to protrude from the distal end 1b of the sheath 1 is enclosed in a protecting member 8, that is, a wrapping layer or tubular member prepared from flexible electrically insulating material.

When the operating wire 6 is moved forward until the abutment 16 contacts the stop 2, the distal end portion 6a of the operating wire 6 which is enclosed in the protecting member 8 is always rendered arcuate, attaining the same effect as the embodiments of FIGS. 14 and 15.

Throughout the foregoing drawings, the same or similar parts are denoted by the same numerals. As used herein, the protecting member 8 and the Teflon tube 12 of FIGS. 11, 12, 20, 21 are all referred to as "wrapping member." Here, the protecting member 8 of the embodiments of FIGS. 5, 9, 13, 15, 17, 19 and 22 need not take a tubular form, but may be prepared simply in the form of layer covering the distal end portion 6a of the operating wire 6.

What is claimed is:

1. A high frequency electrosurgical instrument for cutting human body cavity structures including:
    an electrically insulated sheath having proximal and distal ends;
    a metal wire member extending through the sheath and having a bend which extends from the distal end of the sheath and at which the metal wire member is folded back toward the distal end of the sheath, said metal wire member adapted to be connected to a high frequency source by means for effecting electrical connection therebetween and comprising an operating wire constituted by that portion of the metal wire member which extends through the sheath and which lies between the bend and the proximal end of the sheath and has a distal end portion extendable from the distal end of the sheath, means for reciprocating the operating wire at the proximal end of the sheath, and a cutting wire constituted by that portion of the metal wire member which is folded back toward and lies between the bend and the distal end of the sheath, with one end thereof remote from said bend held by the sheath, said cutting wire being kept substantially straight and fixed in length no matter how far the distal end portion of said operating wire is extended from the distal end of the sheath; and
    an electrically insulated, flexible wrapping member mounted on the distal end portion of the operating wire.

2. The instrument according to claim 1, wherein said metal wire member is provided at said bend with insulative abutting means for abutting against that portion of a first body cavity structure which lies near a second body cavity structure to be cut to prevent the first body cavity structure from being cut with the cutting wire.

3. The instrument according to claim 2, wherein said abutting means comprises an end portion of the wrapping member which covers the bend.

4. The instrument according to claim 2, wherein said abutting means comprises a round-headed cylindrical abutment projectively formed on the bend.

5. The instrument according to claim 2, wherein said abutting means comprises a portion of the wrapping member which is protruded from the bend.

6. The instrument according to claim 5, wherein said wrapping member comprises a tubular member a portion of which is protruded from the bend is provided with holding means for holding the bend.

7. The instrument according to claim 6, wherein said holding means comprises a cut lengthwise formed in the protruded portion of the tubular member and allowing the bend to pass therethrough.

8. The instrument according to claim 6, wherein said holding means comprises a slit lengthwise formed in the protruded portion of the tubular member and allowing the bend to pass therethrough.

9. The instrument according to claim 6, wherein said holding means comprises a hole which is formed in the protruded portion of the tubular member and through which the bend passes.

10. The instrument according to claim 1, further including a stop disposed in the distal end of the sheath and allowing the distal end portion of the operating wire and the cutting wire to reciprocate therethrough, and an engaging member disposed in the sheath and fixed to said one end of the cutting wire, said engaging member abutting against the stop for preventing the cutting wire from slipping off the sheath and for fixing at a predetermined length that portion of the cutting wire which protrudes from the distal end of the sheath no matter how far the distal end portion of the operating wire is extended from the distal end of the sheath.

11. The instrument according to claim 10 wherein said stop comprises a cylindrical stop fixed to an inner wall of the sheath.

12. The instrument according to claim 10 wherein said stop comprises a reduced stepped portion formed in the distal end of the sheath.

13. The instrument according to claim 10, further including an engaging element fixed to an intermediate portion of the operating wire in the sheath, said engaging element being adapted to abut against the stop for restricting the extent to which the distal end portion of the operating wire protrudes from the distal end of the sheath.

14. The instrument according to claim 1, wherein said cutting wire has said one end fixed to the sheath.

15. The instrument according to claim 14, further including a stop fixed in the sheath and allowing the distal end portion of the operating wire to reciprocate therethrough, and an engaging element fixed to that portion of the operating wire which is more remote from the distal end of the sheath than the stop is, said engaging element abutting against the stop for restricting the extent to which the distal end portion of the operating wire protrudes from the distal end of the sheath.

16. The instrument according to claim 1, wherein said wrapping member comprises a tubular layer provided on the distal end portion of the operating wire.

* * * * *